(12) United States Patent
Persichetti et al.

(10) Patent No.: US 8,292,860 B1
(45) Date of Patent: Oct. 23, 2012

(54) MEDICAL DRAINAGE POUCH

(76) Inventors: Gwen C. Persichetti, Suwanee, GA (US); Frank W. Piraino, Laweranceville, GA (US)

( * ) Notice: Subject to any disclaimer, the term of this patent is extended or adjusted under 35 U.S.C. 154(b) by 574 days.

(21) Appl. No.: 12/315,864

(22) Filed: Dec. 8, 2008

(51) Int. Cl.
*A61M 1/00* (2006.01)
*A61F 5/44* (2006.01)
*A45F 3/16* (2006.01)
*A45F 3/20* (2006.01)
*A45F 5/00* (2006.01)

(52) U.S. Cl. ........................................ 604/355
(58) Field of Classification Search .............. 604/317, 604/540, 355, 332, 345; 224/148.1, 602
See application file for complete search history.

(56) References Cited

U.S. PATENT DOCUMENTS

| | | | | |
|---|---|---|---|---|
| 4,073,294 A | * | 2/1978 | Stanley et al. | 604/133 |
| 5,431,701 A | * | 7/1995 | Kagawa et al. | 29/623.2 |
| 5,483,701 A | * | 1/1996 | Ferreyros | 2/49.2 |
| 5,643,233 A | * | 7/1997 | Turner | 604/332 |
| 6,152,915 A | * | 11/2000 | Watson et al. | 604/540 |
| 6,296,164 B1 | * | 10/2001 | Russo | 224/602 |
| 6,390,885 B1 | * | 5/2002 | Brooks | 450/1 |
| 6,524,288 B1 | * | 2/2003 | Hadley-Fruit | 604/322 |
| 6,610,032 B1 | * | 8/2003 | Prody | 604/179 |
| 6,889,407 B2 | * | 5/2005 | Martin | 24/136 R |
| 7,927,311 B1 | * | 4/2011 | Bachelder | 604/179 |
| 2004/0204695 A1 | * | 10/2004 | Bisbee | 604/349 |
| 2006/0206986 A1 | * | 9/2006 | Straiton | 2/238 |
| 2008/0082059 A1 | * | 4/2008 | Fink et al. | 604/305 |
| 2009/0192432 A1 | * | 7/2009 | Frazer | 602/61 |
| 2010/0287681 A1 | * | 11/2010 | Storms et al. | 2/102 |
| 2010/0324532 A1 | * | 12/2010 | Marak et al. | 604/507 |

\* cited by examiner

*Primary Examiner* — Leslie Deak
*Assistant Examiner* — Xin Xie
(74) *Attorney, Agent, or Firm* — Mehrman Law Office; Michael J. Mehrman

(57) ABSTRACT

A medical, post surgery fluid drainage system, such as for use by a mastectomy patient, that allows the wearer/patient to discretely and safely secure and wear the system under clothing. The system includes a mesh fabric pouch having front and rear walls secured together along a bottom edge and along the sides with an open top edge. Inside the pouch are plural fluid receiving bulbs or receptacles. Connected to the bulbs are a like plurality of drain lines or tubes to allow drainage of fluid from plural chest incisions to the bulbs. Further, attachment mechanisms are included to removably secure the pouch to the body of the wearer/patient.

6 Claims, 5 Drawing Sheets

MEDICAL DRAINAGE POUCH

FIELD OF THE INVENTION

This invention is directed to the field of medical devices for use by patients during the period of recovery, more particularly to a medical blood drainage pouch, such as a female patient recovering from a mastectomy.

BACKGROUND OF THE INVENTION

This invention relates to a medical blood drainage device for patients recovering from major surgical procedures that require a closed wound drain system to allow drainage for the patient wearing the device. The device is especially suited as a post mastectomy surgical drainage device, or for other operations, such as liposuction, or any other major surgical procedure that requires a closed wound drain system. The device is constructed of a washable mesh fabric to permit wearing of the device under clothing, and to facilitate washing and showering during the recovery period.

Little is available in the prior art of suitable fluid drain systems to ensure holding of the drain lines in place, preventing pulling of the closed wound which can cause pain and sometimes rips open the closed wound, creating the possibility of emergency care or even infection. However, there is prior art of different aids after medical procedures, where several exemplary devices are illustrated in the following U.S. Patents:

a.) U.S. Pat. No. 7,419,483, to Shrhada, discloses a surgical drain with positioning and protective features having at least one sensor for monitoring and/or recording the condition of the anatomical site or fluid emitted from the site where the surgical drain is placed. It may also include modifications of the surgical drain to improve stabilization or immobilization in the proximity of the anatomical site to be monitored.

b.) U.S. Pat. No. 7,416,543, to Brown et al, covers a drainage bag for receiving bodily waste, such as an ostomy bag, comprising an outer bag of material soluble in cold water, e.g. polyvinyl alcohol, and an inner bag of material insoluble in water ambient temperature and body temperature but soluble in organic solvent, e.g. 2-oxepanone polymer (poly-caprolactone). When the bag and contents are to be disposed of, appropriate organic solvent, such as benzyl alcohol, is applied to the inner bag. The bag can then be placed in a WC bowl and is flushable after 1-2 minutes.

c.) U.S. Pat. No. 7,306,581, to Falconer et al. teaches a drainable ostomy pouch having an outlet. Reinforcing members at the outlet are deformable by application of manual pressure at their ends to distend the outlet. The lateral edges of the reinforcing members may be offset, which encourages the reinforcing members to consistently bend away from each other. A peelable distributed mechanical engagement fastener secures the outlet in a folded condition. The fastener parts are hook-hook type plastic extrusions, and provide a snap-engagement. A security flap is foldable under the outlet when in its folded condition. The outlet is released in two stages.

The prior art falls far short in providing a closed wound fluid drainage system that gives assurance to a wearer/patient of a system that minimizes or avoids premature failure of the drain lines by pulling out of the chest incisions causing possible infection, discomfort and embarrassment to the wearer/patient. The manner by which the present invention achieves these goals will become more apparent in the following specification and accompanying drawings.

SUMMARY OF THE INVENTION

This invention covers a system and kit of components to provide for a medical, post surgery fluid, i.e. blood, drainage system to allow a wearer/patient to discretely and safely secure the system to his/her body. The system comprises a mesh fabric pouch having front and rear walls secured together along a bottom edge and along the respective side walls, open at the top edges. Within the pouch are plural fluid receiving bulbs or receptacles therewithin, a like plurality of drain lines or tubes adapted at first ends to be inserted into chest incisions of the wearer/patient, and at second ends into a respective bulb. Included is a pull cord for restricting the top edge opening of the pouch. Further, means to removably secure the pouch to the wearer/patient in the form of a fabric belt and/or an open ended loop member for securing about the neck of the wearer/patient, the latter particularly suited for showering.

Accordingly, a feature of this invention is the provision of a medical, post surgical fluid drainage system which allows the wearer/patient to discretely and safely under clothing.

Another feature hereof lies in the use of an easily washable and driable pouch for wearing the pouch hereof in a shower.

Still another feature of the invention lies in the use of dual or alternative mechanisms to safely secure the medical pouch to the body of the wearer/patient.

These and other features of the invention will become clearer hereafter from a reading of the following specification and accompanying drawings.

BRIEF DESCRIPTION OF DRAWINGS

FIG. 3A is a front perspective view of a second embodiment of a medical fluid drainage pouch according to this invention.

DETAILED DESCRIPTION OF PREFERRED EMBODIMENT

Figure 1:
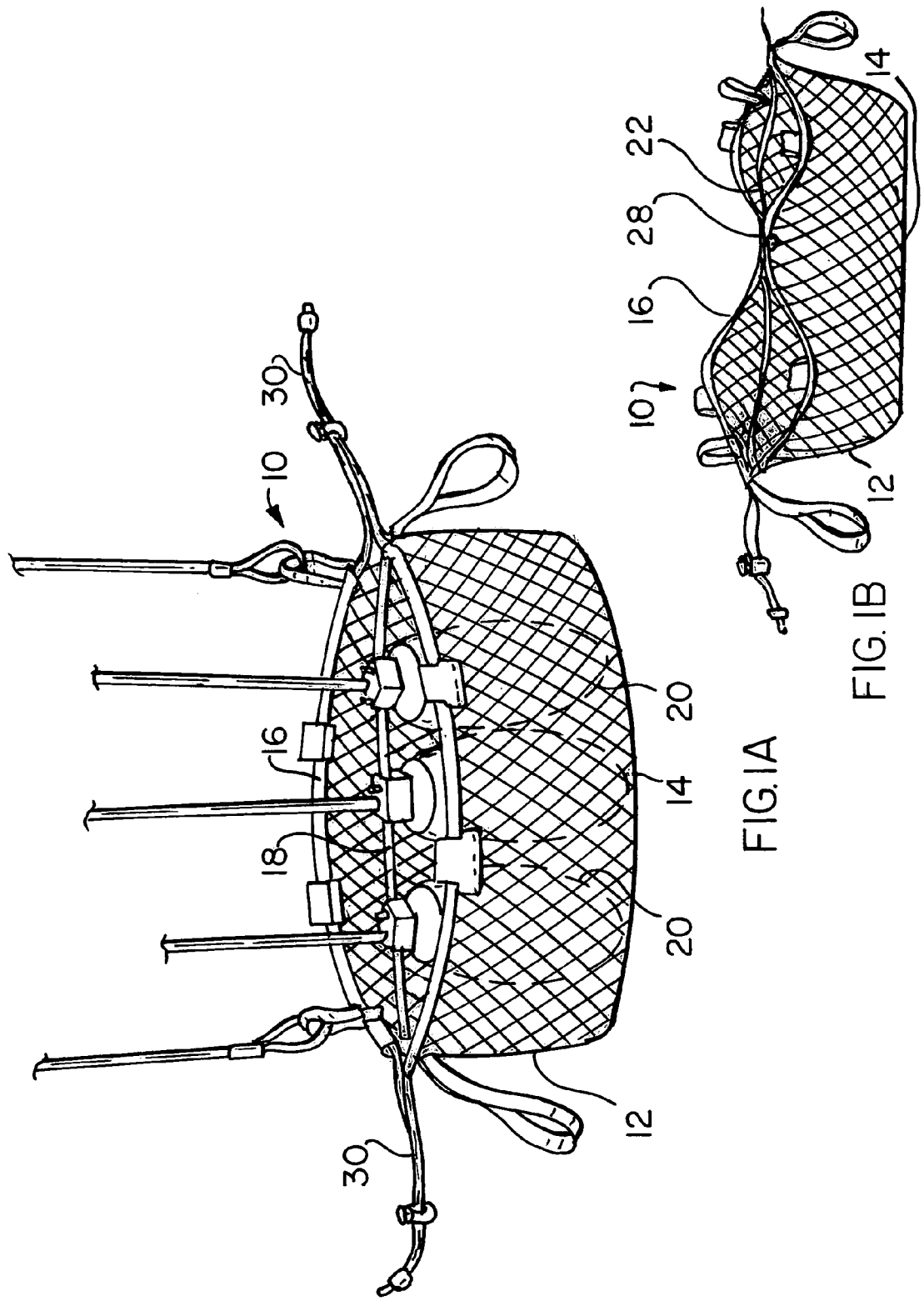
FIGS. 1A and 1B are front perspective views of the medical fluid drainage pouch according to the present invention.

The present invention is directed to a closed wound, surgical fluid drainage system for those patients who have had chest surgery, such as a mastectomy or liposuction, requiring drainage from plural drainage locations. The system is a multi-pouch caddy that allows the wearer thereof to discretely wear the caddy under clothing. The uniqueness of the system will become more apparent in the description which follows, particularly when read in conjunction with the accompanying drawings, where like reference numerals represent like components or features throughout the various views.

Figure 2:
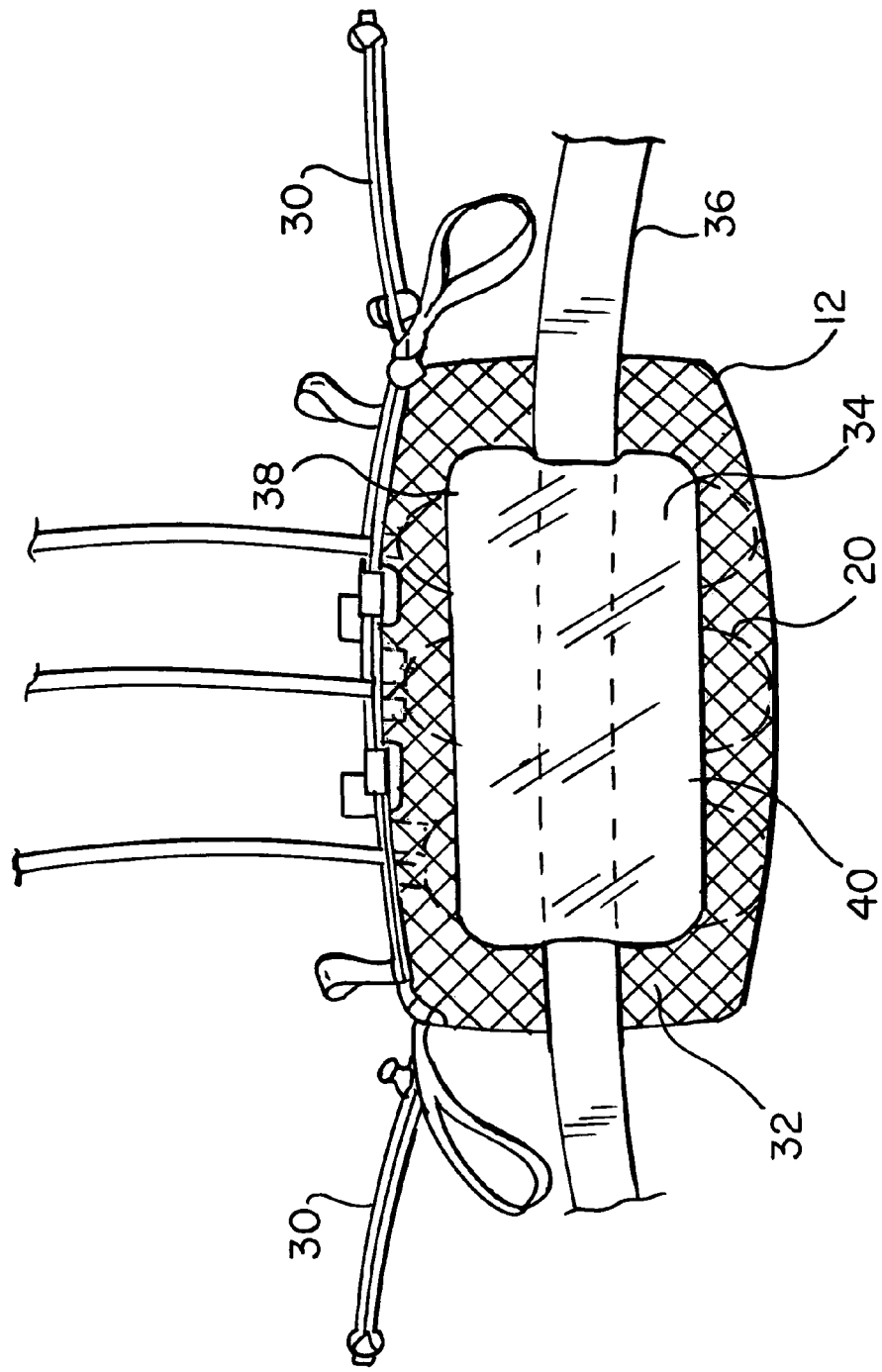
FIG. 2 is a front view of the pouch of FIGS. 1A and 1B showing further a waist belt for securing the pouch to the wearer/patient, a first embodiment for the system hereof.

Turning now to the various Figures, FIGS. 1A, 1B and 2 illustrate a first embodiment for the fluid drainage system 10 of the invention. The system 10 hereof preferably comprises a generally rectangular, fabric mesh pouch 12 with a closed bottom 14 and an open top 16. Preferably the mesh fabric is a PVC/PE so that it may be easily washed and dried. Internally, the pouch may be provided with a pair of secondary intermediate mesh members 18, where opposing said members define plural pockets to receive a like plurality of fluid receiving bulbs 20, see FIG. 1A. Alternately, the pouch may be provided with a longitudinal mesh separator 22, see FIG. 1B. To minimize the profile, the upper edges 26 may be provided with complementary snap members 28, or spot stitched together to temporarily or permanently join the respective edges 26. Further, opposing draw strings 30, one at each end, may be included to close or restrict the pouch opening. Finally, as will be better understood later, a pair of laterally extending loops are provided for attachment to a waist encircling belt, see FIG. 2.

FIG. 2 is a partial back view of the pouch 12 where there is illustrated the back side 32 of the pouch 12 with an opened sided belt loop 34 for slidably receiving a belt 36, with the upper and lower edges 38, 40, respectively, sewn to the mesh fabric. Since wearing something close to the body, particularly the mesh fabric, the outer face of the loop 34 may comprise a smooth, body friendly material to prevent irritation to the skin of the wearer/patient. The belt 36, preferably a thin fabric, may be secured by hook and pile fasteners, also known commercially as VELCRO fasteners, as known in the art. As an alternate to the illustrated single belt loop 34, plural belt loops may be used.

Figures 3A, 3B:
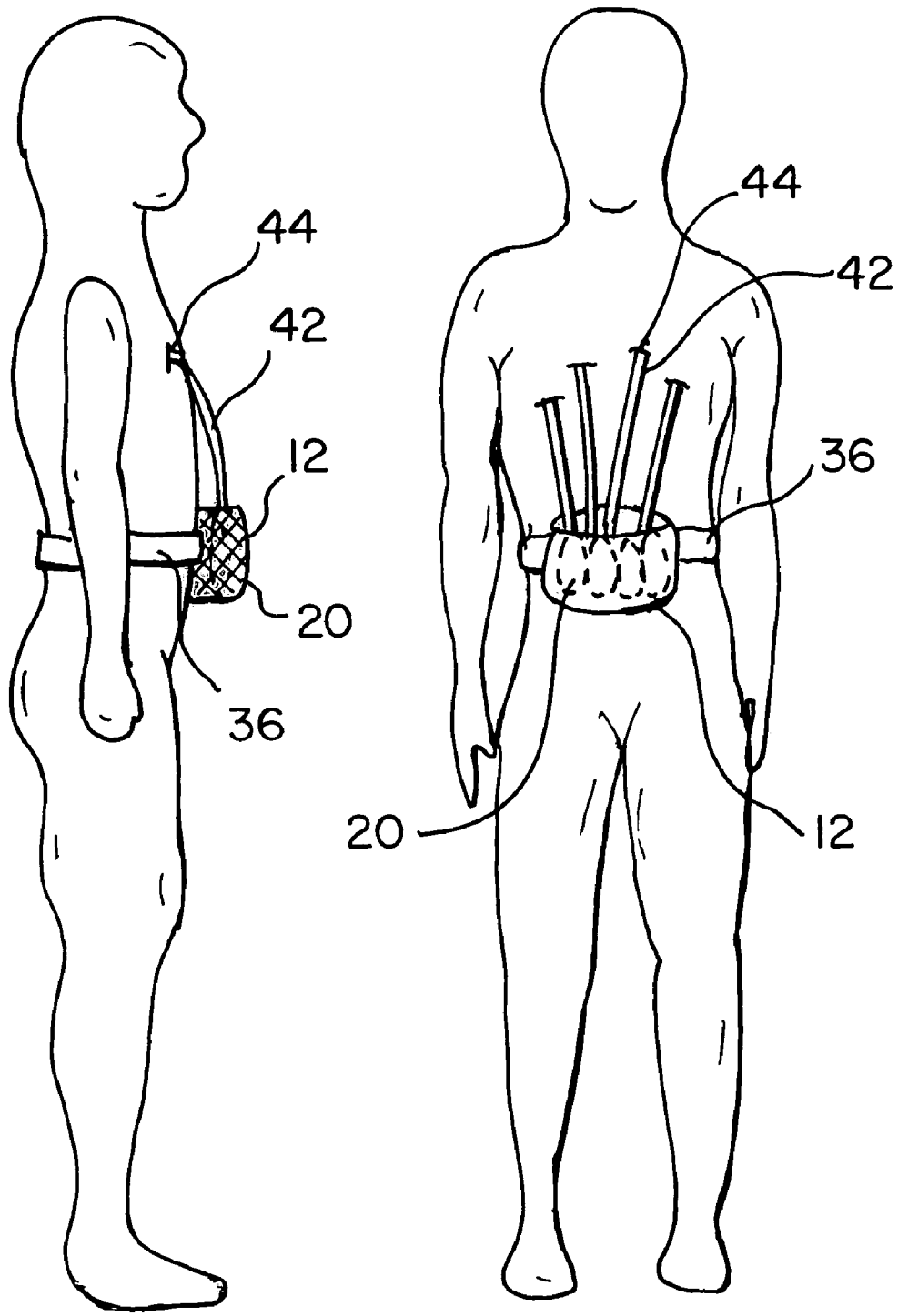
FIGS. 3A and 3B are front and side views, respectively, showing a wearer/patient wearing the pouch hereof of FIG. 2.

FIGS. 3A and 3B illustrate two views for a first embodiment of a wearer/patient wearing the pouch secured by the belt 36. Further, to help illustrate the function of the pouch during its use, the wearer/patient is shown with plural fluid drain lines 42, or tubes, conduits, etc., extending from chest incisions 44 to a complementary fluid receiving bulb 20. By this arrangement the wearer/patient can discretely have the secured pouch under clothing without the appearance of same under the clothing.

Figure 4:
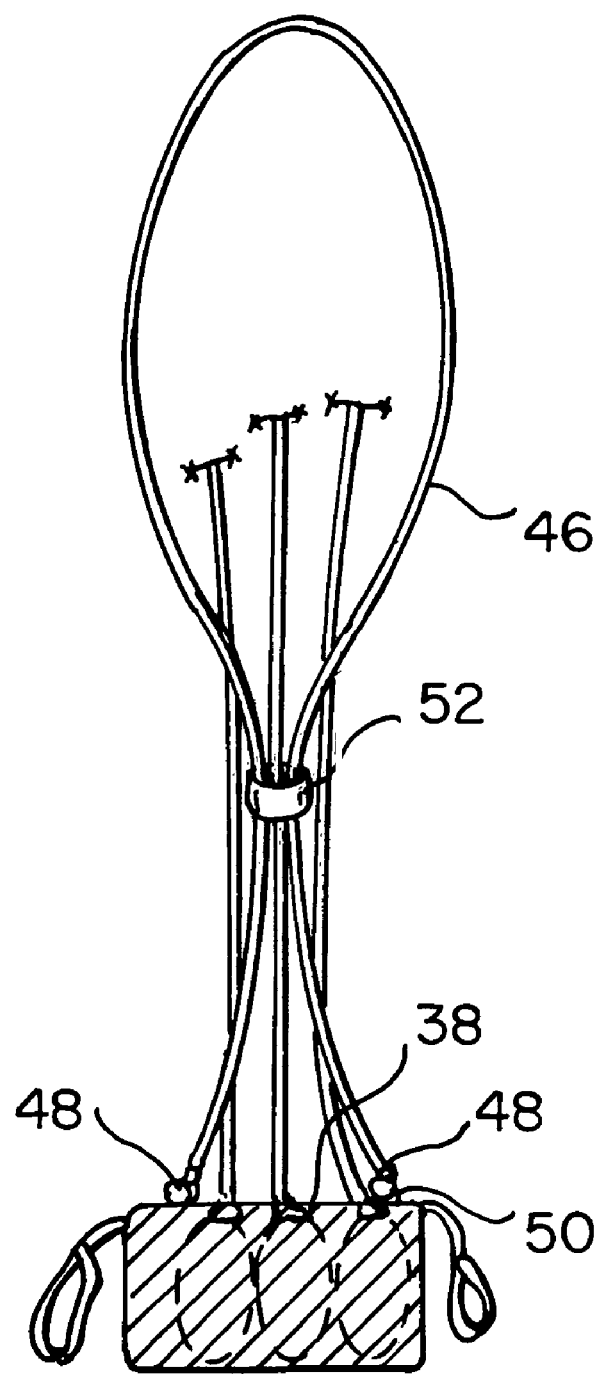
FIG. 4 is a partial front view of an adjustable neck strap representing a second embodiment, to allow the wearer/patient to wear the pouch according to the invention.
Figures 5A, 5B:
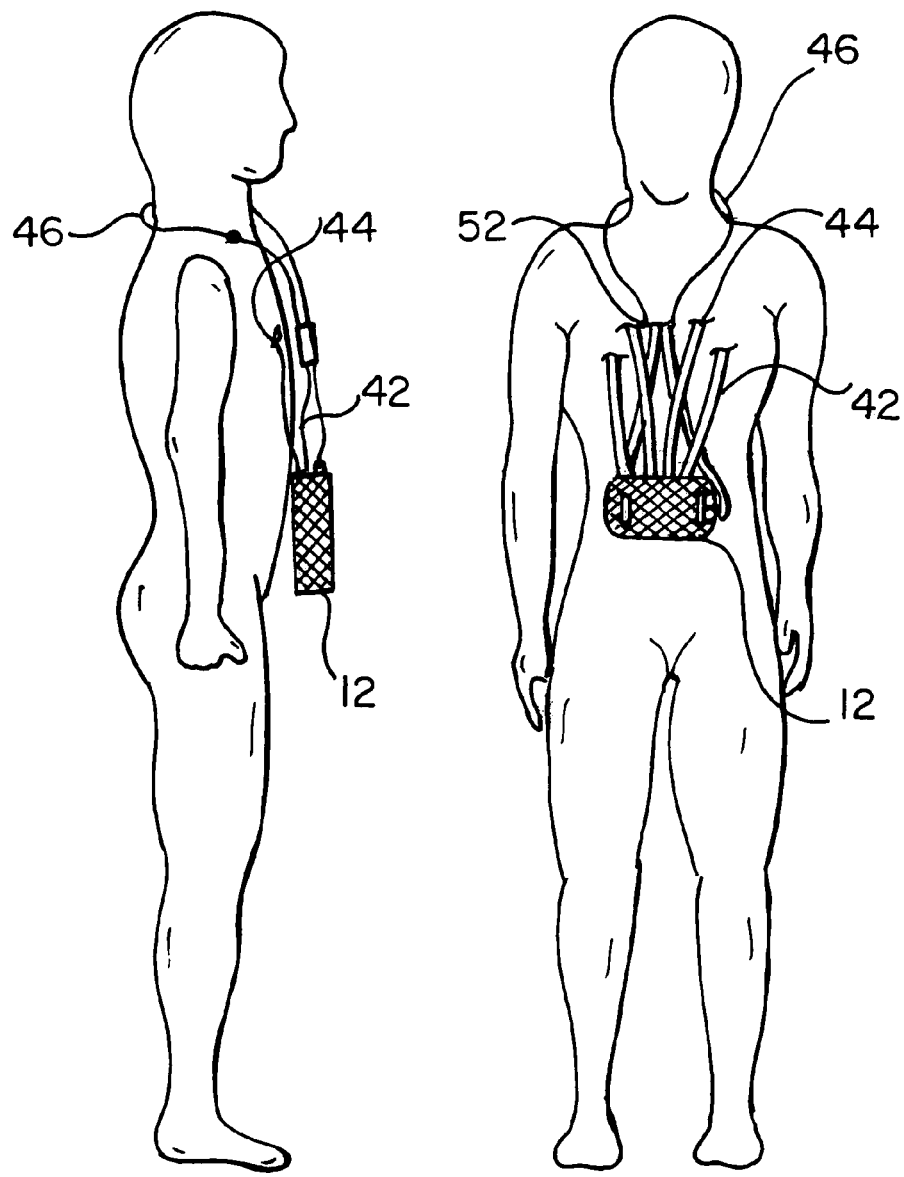
FIG. 5A is a front view similar to FIG. 3A of a patient/wearer wearing the pouch by means of the adjustable neck strap of FIG. 4.
FIG. 5B is a side view of the second embodiment of FIG. 4.

FIGS. 4, 5A and 5B illustrate a second embodiment showing an alternate manner of securing the pouch 12 to a wearer/patient, where such alternate manner is particularly suited for taking a shower. As best seen in FIG. 4, this second embodiment comprises an open looped member 46 having a pair of free ends 48 with means to removably attach same to complementary loops 50 along the upper edge 38. Also, for adjusting the length of the looped member 46, a slide member 52 may be provided. In this embodiment, as well as the belt system, the wearer/patient will be comfortable in knowing that a secure and safe system has been found that minimizes or avoids premature removal of the drainage lines or conduits.

It is recognized that changes, variations and modifications may be made to the medical surgical drainage system of this invention without departing from the spirit and scope thereof. Accordingly, no limitation is intended to be imposed thereon except as set forth in the accompanying claims.

We claim:

1. A medical, post surgery fluid drainage system to allow a wearer/patient to discretely and safely secure the system to his/her body and facilitate showering, said system comprising:
    a pouch configured for holding one or more body drainage receptacles connected to one or more drain lines connected to incisions of the wearer/patient;
    a waist belt configured to be connected to and removed from the pouch sized for securely supporting the pouch under clothing of the wearer/patient;
    a neck loop, separate from the waist belt, configured to be connected to and removed from the pouch sized for loosely hanging the pouch from the neck of wearer/patient; and
    wherein the waist belt is sized to securely support the pouch to the waist under clothes worn by the wearer/patient when the is wearer/patient not showering; and
    wherein the neck loop is sized to hang the pouch from the neck of the wearer/patient more loosely than the waist secures the pouch to the waist of the wearer/patient to allow the pouch to articulate away from the body to accommodate showering.

2. The medical, post surgery fluid drainage system according to claim 1, further comprising means for restricting the top edge opening of said pouch comprises at least one sliding pull cord with a locking member.

3. The medical, post surgery fluid drainage system according to claim 1, further comprising a first fastener for removably connecting the waist belt to the pouch and a second fastener, separate from the first fastener, for removably connecting the neck loop to the pouch.

4. The medical, post surgery fluid drainage system according to claim 3 wherein the first fastener comprises one or more belt loops.

5. The medical, post surgery fluid drainage system according to claim 4, wherein the second fastener comprises a pair of loops attached at or near opposing ends of the pouch.

6. The medical, post surgery fluid drainage system according to claim 1, including mesh separators within said pouch, where said separators are joined at spaced apart locations to define plural pockets for receiving multiple body drainage receptacles.

* * * * *